(12) United States Patent
Erickson et al.

(10) Patent No.: US 7,151,163 B2
(45) Date of Patent: Dec. 19, 2006

(54) ANTIVIRAL AGENTS FOR THE TREATMENT, CONTROL AND PREVENTION OF INFECTIONS BY CORONAVIRUSES

(75) Inventors: John W. Erickson, Potomac, MD (US); Abelardo Silva, Ellicott City, MD (US)

(73) Assignee: Sequoia Pharmaceuticals, Inc., Gaithersburg, MD (US)

( * ) Notice: Subject to any disclaimer, the term of this patent is extended or adjusted under 35 U.S.C. 154(b) by 0 days.

(21) Appl. No.: 10/833,304

(22) Filed: Apr. 28, 2004

(65) Prior Publication Data

US 2006/0258577 A1   Nov. 16, 2006

Related U.S. Application Data

(60) Provisional application No. 60/466,432, filed on Apr. 30, 2003, provisional application No. 60/465,782, filed on Apr. 28, 2003.

(51) Int. Cl.
  *C07K 14/165* (2006.01)
  *C07K 17/00* (2006.01)
  *A61K 39/215* (2006.01)
  *A61K 39/385* (2006.01)

(52) U.S. Cl. ............... 530/363; 514/12; 424/186.1; 424/196.11; 424/221.1; 424/192.1

(58) Field of Classification Search ............ 514/12–16, 514/2; 530/324–329, 363, 402; 424/186.1, 424/196.11, 221.1, 192.1
See application file for complete search history.

(56) References Cited

U.S. PATENT DOCUMENTS

| | | | |
|---|---|---|---|
| 3,431,194 A | 3/1969 | Bartok et al. | |
| 4,080,397 A | 3/1978 | Derr et al. | |
| 5,378,348 A | 1/1995 | Davis et al. | |
| 5,888,376 A | 3/1999 | Wittenbrink et al. | |
| 6,436,278 B1 | 8/2002 | Bennazzi et al. | |
| 2004/0071709 A1* | 4/2004 | Rottier et al. | 424/159.1 |
| 2004/0180380 A1* | 9/2004 | Lee et al. | 435/7.1 |
| 2004/0229219 A1* | 11/2004 | Gallaher et al. | 435/5 |

FOREIGN PATENT DOCUMENTS

| | | | |
|---|---|---|---|
| EP | 323092 A2 | | 7/1989 |
| EP | 583836 A1 | | 2/1994 |
| WO | WO 01/34186 | * | 5/2001 |

OTHER PUBLICATIONS

Osborn et al. Journal of Pharmacology and Experimental Therapeutics 303(2): 540-548, 2002.*
Liu et al (Lancet 363:938-947, Mar. 20, 2004).*
Kliger et al (BMC Microbiology 3:20, Sep. 21, 2003). [online] [retrieved on May 18, 2005] Retreived from the Internet <http://www.biomedcentral.com/1471-2180/3/20>.*
Gustchina et al (J. Med. Chem. 48:3036-3044, 2005).*
Veiga et al (BBA 1760:55-61, 2006).*
Lip et al (Journal of Virology 80:941-950, 2006).*

* cited by examiner

*Primary Examiner*—Mary E. Mosher
(74) *Attorney, Agent, or Firm*—Proskauer Rose LLP

(57) ABSTRACT

The invention provides compositions and methods that are useful for preventing and treating a coronavirus infection in a subject. More specifically, the invention provides peptides and conjugates and pharmaceutical compositions containing those peptides and conjugates that block fusion of a coronavirus, such as the SARS virus, to a target cell. This blocking mechanism prevents or treats a coronavirus infection, such as a SARS infection, in a subject, such as a human subject.

8 Claims, 2 Drawing Sheets

Figure 2

```
C-terminal, HR2 peptide 1
svVNIQKEIDRLNEVAKNLNESLIDLQELGkyeqyik
EEEE HHHHHHHHHHHHHHHH    HHHH    EEEE
13304135766888888642110022442002002 31
ohLslpsEhsRlptsIcsLNpShINLcpluphEhYVK N-Terminal, HR1 peptide 2
QIPFAMQMAYRFNGIGVTQNVLYENQKQIANQFNKAISQIQESLT
.LL..HHHHHHH......HHHHHH.HHHHHHHHHHHHHHH.....
26523566776632000155776647888888677776542003
1PFhlsVQhRINtlGlThsVLspNQchIAsAFNpAlssIQEGFc
```

ANTIVIRAL AGENTS FOR THE TREATMENT, CONTROL AND PREVENTION OF INFECTIONS BY CORONAVIRUSES

This application claims the benefit of U.S. Provisional Application No. 60/466,432, filed Apr. 30, 2003, and U.S. Provisional Application No. 60/465,782, filed Apr. 28, 2003. The entire contents of each of the above-identified applications are hereby incorporated by reference.

BACKGROUND

Severe Acute Respiratory Syndrome (SARS) is an emerging new infectious disease caused by a novel coronavirus that infects humans. See Ksiazek et al., *New Engl. J. Med.* (http://content.nejm.org/cgi/reprint/NEJMoa030781 v2.pdf, published Apr. 10, 2003). SARS is fatal in about 4–10% of cases reported so far. Initially described in mid February, 2003 in China's Guangdong province as atypical pneumonia, by mid-March, 2003 the World Health Organization (WHO) had received reports of more than 150 new suspected cases of unknown origin or cause. By mid April, 2003, over 4400 cases with 263 deaths of patients diagnosed with symptoms of SARS have been documented from 26 different countries, including Canada, China, Hong Kong, Indonesia, Philippines, Singapore, Thailand, Viet Nam and the United States. In light of the rapid spread of SARS to several countries in a short period of time, the World Health Organization issued a global alert and provided emergency guidance for travellers and airlines. In only a few months after the outbreak was first recognized, SARS became a worldwide threat to global health and global economies. There are presently no known therapies that are effective against SARS, and no vaccine is available. Accordingly, there is an urgent need for antiviral agents that can control or prevent SARS in infected individuals, and that can prevent SARS from spreading.

In general, SARS begins with a fever greater than 100.4° F. [>38.0° C.]. Other symptoms may include headache, an overall feeling of discomfort, and body aches. Some people also experience mild respiratory symptoms. After 2 to 7 days, SARS patients may develop a dry cough and have trouble breathing.

The primary way that SARS appears to spread is by close person-to-person contact. Most cases of SARS have involved people who cared for or lived with someone with SARS, or had direct contact with infectious material (for example, respiratory secretions) from a person who has SARS. Potential ways in which SARS can be spread include touching the skin of other people or objects that are contaminated with infectious droplets followed by touching of eye(s), nose, or mouth. This can happen when someone who is sick with SARS coughs or sneezes droplets onto themselves, other people, or nearby surfaces. It also is possible that SARS can be spread more broadly through the air or by other ways that are currently not known.

Scientists at the Centers for Disease Control and Prevention (CDC) and other laboratories around the world have detected a previously unrecognized coronavirus in patients with SARS. The evidence for a coronavirus was based on genetic fingerprint and electron microscopic ultrastructural studies and was widely reported in the popular press. Viologists at the CDC, WHO and numerous academic laboratories all reported that a coronavirus is the leading hypothesis for the cause of SARS.

The CDC recently reported sequencing the genome for SARS-CoV (Urbani strain), a strain of a novel human coronavirus believed to be responsible for SARS. The sequence data confirm that the SARS virus is a previously unrecognized coronavirus. The virus was cultured from cells taken from a throat culture taken from a SARS patients and grown in Vero cells (African green monkey kidney cells) in order to reproduce the ribonucleic acid (RNA) of the disease-causing coronavirus. The new sequence has 29,727 nucleotides, which places it well within the typical RNA boundaries for coronaviruses. Members of this viral family tend to have between 29,000 and 31,000 nucleotides. See Lai et al., *Adv. Virus Res.* 48:1, (1997). The genome organization of the SARS virus also is similar to that of other coronaviruses.

The genome sequence of SARS-CoV (Urbani) is available from GenBank at the Web site for the National Center for Biotechnology Information, National Library of Medicine http://www.ncbi.nim.nih.gov/. The accession number for the sequence of SARS-CoV (Urbani strain) is ay278741. The present inventors have used these sequence data to identify molecular targets that can be exploited to design safe and effective novel antiviral therapies that can be used to treat SARS and to stem the tide of the growing epidemic.

SUMMARY OF THE INVENTION

In accordance with a first aspect of the invention there is provided an antiviral peptide having between 7 and 50 amino acids, where the peptide exhibits antiviral activity against a coronavirus, and where the peptide contains a sequence comprising at least 7 contiguous amino acids from one of the following sequences:

DVDLGDISGINASVVNIQKEIDRLNE-VAKNLNESLIDLQELGKYEQYIK (SEQ ID NO: 1);

QIPFAMQMAYRFNGIGVTQNVLYENQK-QIANQFNKAISQIQESLT (SEQ ID NO: 2);

ESLTTSTALGKLQDVVN-QNAQALNTLVKQLSSNFGAISS (SEQ ID NO: 3);

GKLQDVVNQNAQALNTLVKQLSSNF-GAISSVLNDILSRLDKVEAE (SEQ ID NO: 4); and

RLITGRLQSLQTYVTQQLIRAAEI-RASANLAATKMSECVLGQSKRVDF (SEQ ID NO: 5).

In accordance with a second aspect of the invention there is provided an antiviral peptide having between 7 and 50 amino acids, where the peptide exhibits antiviral activity against a coronavirus, and where the peptide contains a sequence comprising at least 7 contiguous amino acids from the sequence:

DV<u>D</u>LG<u>D</u>ISG<u>I</u>NAS<u>VV</u>NIQKE<u>I</u>DRL<u>NE</u>V<u>A</u>KN<u>L</u>NES LIDLQE<u>LG</u>K<u>Y</u>EQYIK (SEQ ID NO: 1);

where the amino acids at bold letter positions can be substituted with an amino acid selected from the group consisting of I, L, V, W, Y, F, N, Q, S, T, D, E, G, H, and M, and where amino acids in non-bold positions can be any amino acid except proline.

| | |
|---|---|
| SVVNIQK | (SEQ ID NO:6) |
| VVNIQKE | (SEQ ID NO:7) |
| VNIQKEI | (SEQ ID NO:8) |
| NIQKEID | (SEQ ID NO:9) |
| IQKEIDR | (SEQ ID NO:10) |
| QKEIDRL | (SEQ ID NO:11) |

-continued

| | | | | |
|---|---|---|---|---|
| KEIDRLN | (SEQ ID NO:12) | | VTQNVLY | (SEQ ID NO:52) |
| EIDRLNE | (SEQ ID NO:13) | | TQNVLYE | (SEQ ID NO:53) |
| IDRLNEV | (SEQ ID NO:14) | | QNVLYEN | (SEQ ID NO:54) |
| DRLNEVA | (SEQ ID NO:15) | | NVLYENQ | (SEQ ID NO:55) |
| RLNEVAK | (SEQ ID NO:16) | | VLYENQK | (SEQ ID NO:56) |
| LNEVAKN | (SEQ ID NO:17) | | LYENQKQ | (SEQ ID NO:57) |
| NEVAKNL | (SEQ ID NO:18) | | YENQKQI | (SEQ ID NO:58) |
| EVAKNLN | (SEQ ID NO:19) | | ENQKQIA | (SEQ ID NO:59) |
| VAKNLNE | (SEQ ID NO:20) | | NQKQIAN | (SEQ ID NO:60) |
| AKNLNES | (SEQ ID NO:21) | | QKQIANQ | (SEQ ID NO:61) |
| KNLNESL | (SEQ ID NO:22) | | KQIANQF | (SEQ ID NO:62) |
| NLNESLI | (SEQ ID NO:23) | | QIANQFN | (SEQ ID NO:63) |
| LNESLID | (SEQ ID NO:24) | | IANQFNK | (SEQ ID NO:64) |
| NESLIDL | (SEQ ID NO:25) | | ANQFNKA | (SEQ ID NO:65) |
| ESLIDLQ | (SEQ ID NO:26) | | NQFNKAI | (SEQ ID NO:66) |
| SLIDLQE | (SEQ ID NO:27) | | QFNKAIS | (SEQ ID NO:67) |
| LIDLQEL | (SEQ ID NO:28) | | FNKAISQ | (SEQ ID NO:68) |
| IDLQELG | (SEQ ID NO:29) | | NKAISQI | (SEQ ID NO:69) |
| DLQELGK | (SEQ ID NO:30) | | KAISQIQ | (SEQ ID NO:70) |
| LQELGKY | (SEQ ID NO:31) | | AISQIQE | (SEQ ID NO:71) |
| QELGKYE | (SEQ ID NO:32) | | ISQIQES | (SEQ ID NO:72) |
| ELGKYEQ | (SEQ ID NO:33) | | SQIQESL | (SEQ ID NO:73) |
| LGKYEQY | (SEQ ID NO:34) | | QIQESLT | (SEQ ID NO:74) |
| GKYEQYI | (SEQ ID NO:35) | | ESLTTTS | (SEQ ID NO:75) |
| KYEQYIK | (SEQ ID NO:36) | | SLTTTST | (SEQ ID NO:76) |
| QIPFAMQ | (SEQ ID NO:37) | | LTTTSTA | (SEQ ID NO:77) |
| IPFAMQM | (SEQ ID NO:38) | | TTTSTAL | (SEQ ID NO:78) |
| PFAMQMA | (SEQ ID NO:39) | | TTSTALG | (SEQ ID NO:79) |
| FAMQMAY | (SEQ ID NO:40) | | TSTALGK | (SEQ ID NO:80) |
| AMQMAYR | (SEQ ID NO:41) | | STALGKL | (SEQ ID NO:81) |
| MQMAYRF | (SEQ ID NO:42) | | TALGKLQ | (SEQ ID NO:82) |
| QMAYRFN | (SEQ ID NO:43) | | ALGKLQD | (SEQ ID NO:83) |
| MAYRFNG | (SEQ ID NO:44) | | LGKLQDV | (SEQ ID NO:84) |
| AYRFNGI | (SEQ ID NO:45) | | GKLQDVV | (SEQ ID NO:85) |
| YRFNGIG | (SEQ ID NO:46) | | KLQDVVN | (SEQ ID NO:86) |
| RFNGIGV | (SEQ ID NO:47) | | LQDVVNQ | (SEQ ID NO:87) |
| FNGIGVT | (SEQ ID NO:48) | | QDVVNQN | (SEQ ID NO:88) |
| NGIGVTQ | (SEQ ID NO:49) | | DVVNQNA | (SEQ ID NO:89) |
| IGVTQNV | (SEQ ID NO:50) | | VVNQNAQ | (SEQ ID NO:90) |
| GVTQNVL | (SEQ ID NO:51) | | VNQNAQA | (SEQ ID NO:91) |

| | | | | |
|---|---|---|---|---|
| NQNAQAL | (SEQ ID NO:92) | | GAISSVL | (SEQ ID NO:132) |
| QNAQALN | (SEQ ID NO:93) | | AISSVLN | (SEQ ID NO:133) |
| NAQALNT | (SEQ ID NO:94) | | ISSVLND | (SEQ ID NO:134) |
| AQALNTL | (SEQ ID NO:95) | | SSVLNDI | (SEQ ID NO:135) |
| QALNTLV | (SEQ ID NO:96) | | SVLNDIL | (SEQ ID NO:136) |
| ALNTLVK | (SEQ ID NO:97) | | VLNDILS | (SEQ ID NO:137) |
| LNTLVKQ | (SEQ ID NO:98) | | LNDILSR | (SEQ ID NO:138) |
| NTLVKQL | (SEQ ID NO:99) | | NDILSRL | (SEQ ID NO:139) |
| TLVKQLS | (SEQ ID NO:100) | | DILSRLD | (SEQ ID NO:140) |
| LVKQLSS | (SEQ ID NO:101) | | ILSRLDK | (SEQ ID NO:141) |
| VKQLSSN | (SEQ ID NO:102) | | LSRLDK | (SEQ ID NO:142) |
| KQLSSNF | (SEQ ID NO:103) | | SRLDKV | (SEQ ID NO:143) |
| QLSSNFG | (SEQ ID NO:104) | | RLDKVE | (SEQ ID NO:144) |
| LSSNFGA | (SEQ ID NO:105) | | LDKVEA, | (SEQ ID NO:145) |
| SSNFGAI | (SEQ ID NO:106) | | RLITGRL | (SEQ ID NO:146) |
| SNFGAIS | (SEQ ID NO:107) | | LITGRLQ | (SEQ ID NO:147) |
| NFGAISS | (SEQ ID NO:108) | | ITGRLQS | (SEQ ID NO:148) |
| LQDVVNQ | (SEQ ID NO:109) | | TGRLQSL | (SEQ ID NO:149) |
| QDVVNQN | (SEQ ID NO:110) | | GRLQSLQ | (SEQ ID NO:150) |
| DVVNQNA | (SEQ ID NO:111) | | RLQSLQT | (SEQ ID NO:151) |
| VVNQNAQ | (SEQ ID NO:112) | | LQSLQTY | (SEQ ID NO:152) |
| VNQNAQA | (SEQ ID NO:113) | | QSLQTYV | (SEQ ID NO:153) |
| NQNAQAL | (SEQ ID NO:114) | | SLQTYVT | (SEQ ID NO:154) |
| QNAQALN | (SEQ ID NO:115) | | LQTYVTQ | (SEQ ID NO:155) |
| NAQALNT | (SEQ ID NO:116) | | QTYVTQQ | (SEQ ID NO:156) |
| AQALNTL | (SEQ ID NO:117) | | TYVTQQL | (SEQ ID NO:157) |
| QALNTLV | (SEQ ID NO:118) | | YVTQQLI | (SEQ ID NO:158) |
| ALNTLVK | (SEQ ID NO:119) | | VTQQLIR | (SEQ ID NO:159) |
| LNTLVKQ | (SEQ ID NO:120) | | TQQLIRA | (SEQ ID NO:160) |
| NTLVKQL | (SEQ ID NO:121) | | QQLIRAA | (SEQ ID NO:161) |
| TLVKQLS | (SEQ ID NO:122) | | QLIRAAE | (SEQ ID NO:162) |
| LVKQLSS | (SEQ ID NO:123) | | LIRAAEI | (SEQ ID NO:163) |
| VKQLSSN | (SEQ ID NO:124) | | IRAAEIR | (SEQ ID NO:164) |
| KQLSSNF | (SEQ ID NO:125) | | RAAEIRA | (SEQ ID NO:165) |
| QLSSNFG | (SEQ ID NO:126) | | AAEIRAS | (SEQ ID NO:166) |
| LSSNFGA | (SEQ ID NO:127) | | AEIRASA | (SEQ ID NO:167) |
| SSNFGAI | (SEQ ID NO:128) | | EIRASAN | (SEQ ID NO:168) |
| SNFGAIS | (SEQ ID NO:129) | | IRASANL | (SEQ ID NO:169) |
| NFGAISS | (SEQ ID NO:130) | | RASANLA | (SEQ ID NO:170) |
| FGAISSV | (SEQ ID NO:131) | | ASANLAA | (SEQ ID NO:171) |

```
               -continued
    SANLAAT            (SEQ ID NO:172)

ANLAATK            (SEQ ID NO:173)

NLAATKM            (SEQ ID NO:174)

LAATKMS            (SEQ ID NO:175)

AATKMSE            (SEQ ID NO:176)

ATKMSEC            (SEQ ID NO:177)

TKMSECV            (SEQ ID NO:178)

KMSECVL and        (SEQ ID NO:179)

MSECVLG.           (SEQ ID NO:180)
```

The peptide may contain at least 10, 15, 20, 25, 30, 35, or 40 contiguous amino acids from one of the sequences:

VVNIQKEIDRLNEVAKNLNESLIDLQELGKYEQYIK (SEQ ID NO: 181);

QIPFAMQMAYRFNGIGVTQNVLYENQK-QIANQFNKAISQIQESLT (SEQ ID NO: 2);

ESLTTTSTALGKLQDVVN-QNAQALNTLVKQLSSNFGAISS (SEQ ID NO: 3);

GKLQDVVNQNAQALNTLVKQLSSNF-GAISSVLNDILSRLDKVEAE (SEQ ID NO: 4); and

RLITGRLQSLQTYVTQQLIRAAEI-RASANLAATKMSECVLGQSKRVDF (SEQ ID NO: 5).

Any of the peptides above may be linked to a carrier protein, such as human serum albumin, for example.

In accordance with a third aspect of the invention there is provided an antiviral composition comprising a peptide X having between 7 and 50 amino acids, where the peptide exhibits antiviral activity against a coronavirus, and where the composition has the structure:

B—X—Z, where B is an amino acid sequence containing up to about 43 amino acids, or B is an amino group, an acetyl group, a 9-fluorenylmethoxy-carbonyl group, a hydrophobic group, or a macromolecule carrier group, or B is a carrier protein, in which case B may contain more than 8 amino acids, and may also comprises a linker peptide sequence that connects the antiviral sequence to the carrier protein; Z is an amino acid sequence containing up to about 43 amino acids, or Z comprises a carboxyl group, an amido group, a hydrophobic group, or a macromolecular carrier group, or Z is a carrier protein, such as HSA, in which case Z may contain more than 8 amino acids, and may also comprise a linker peptide sequence that connects the antiviral sequence to the carrier protein; where when considered together B and Z must contain at least 8 amino acids between the B and Z groups; and where X is a peptide sequence comprising at least 7 contiguous amino acids from one of the following sequences:

VVNIQKEIDRLNEVAKNLNESLIDLQELGKYEQYIK (SEQ ID NO: 181);

QIPFAMQMAYRFNGIGVTQNVLYENQK-QIANQFNKAISQIQESLT (SEQ ID NO: 2);

ESLTTTSTALGKLQDVVN-QNAQALNTLVKQLSSNFGAISS (SEQ ID NO: 3);

GKLQDVVNQNAQALNTLVKQLSSNF-GAISSVLNDILSRLDKVEAE (SEQ ID NO: 4); and

RLITGRLQSLQTYVTQQLIRAAEI-RASANLAATKMSECVLGQSKRVDF (SEQ ID NO: 5).

X may contain, for example, at least 10, 15, 20, 25, 30, 35, or 40 contiguous amino acids from one of the following sequences:

VVNIQKEIDRLNEVAKNLNESLIDLQELGKYEQYIK (SEQ ID NO: 181);

QIPFAMQMAYRFNGIGVTQNVLYENQK-QIANQFNKAISQIQESLT (SEQ ID NO: 2);

ESLTTTSTALGKLQDVVN-QNAQALNTLVKQLSSNFGAISS (SEQ ID NO: 3);

GKLQDVVNQNAQALNTLVKQLSSNF-GAISSVLNDILSRLDKVEAE (SEQ ID NO: 4); and

RLITGRLQSLQTYVTQQLIRAAEI-RASANLAATKMSECVLGQSKRVDF (SEQ ID NO: 5).

In accordance with a fourth aspect of the invention there is provided an antiviral peptide having between 7 and 50 amino acids, where the peptide exhibits antiviral activity against a coronavirus, and where the peptide comprises a sequence that exhibits identity in any two of the seven positions of a contiguous heptapeptide, where the contiguous heptapeptide comprises 7 contiguous amino acids from one of the following sequences:

VVNIQKEIDRLNEVAKNLNESLIDLQELGKYEQYIK (SEQ ID NO: 181);

QIPFAMQMAYRFNGIGVTQNVLYENQK-QIANQFNKAISQIQESLT (SEQ ID NO: 2);

ESLTTTSTALGKLQDVVN-QNAQALNTLVKQLSSNFGAISS (SEQ ID NO: 3);

GKLQDVVNQNAQALNTLVKQLSSNF-GAISSVLNDILSRLDKVEAE (SEQ ID NO: 4); and

RLITGRLQSLQTYVTQQLIRAAEI-RASANLAATKMSECVLGQSKRVDF (SEQ ID NO: 5).

The sequence identity may be located, for example, in the ith and i+4th positions in the contiguous heptapeptides.

In accordance with another aspect of the invention there is provided a pharmaceutical composition comprising a peptide or composition as described above and a pharmaceutically acceptable diluent, adjuvant and/or excipient.

In accordance with yet another aspect of the invention there is provided a method of treating or preventing a coronavirus infection in a subject, comprising administering to a patient suspected of suffering from the infection an effective amount of a peptide or composition as described above. The subject may be a human, a cow, pig, or chicken.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 2 shows some representative examples of results of secondary structure prediction and homology analyses on peptides (SEQ ID NOS 197 and 2, respectively in order of appearance) from SARS coronavirus, isolate Tor2, E2 glycoprotein precursor. Amino acids in the most highly predicted helical regions are listed in bold. E, H and L designations are from the secondary structure prediction algorithm and refer to extended or coil, helix and loop regions, respectively. Numbers refer to the probable accuracy of the prediction, from lowest (0) to highest (9).

DESCRIPTION OF THE INVENTION

Figure 1:
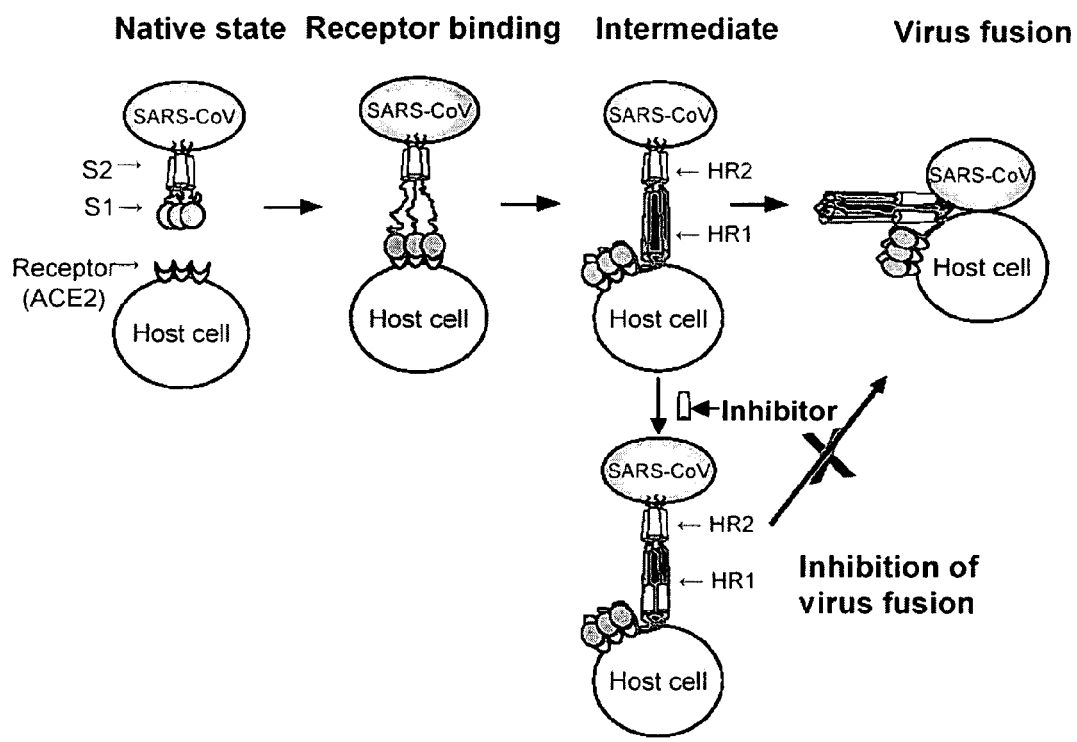
FIG. 1 shows a model of SARS-CoV fusing with the host cell and of an inhibitor blocking fusion between SARS-CoV and the host cell membrane. SARS-CoV contains a surface spike protein consisting of S1 and S2 domains. SARS-CoV binds to the host cell through interaction between S1 domain and the host cell receptor, ACE2. The HR2 helices of the S2 protein fold over and interact with the HR1 helices to form "hairpin-like" structures, which draw both the viral and host cell membranes together for fusion. An inhibitor is shown in the lower portion binding to the HR1 trimer and blocking association of HR1 and HR2, thereby inhibiting SARSCoV fusion with the host cell. Model from www.nybloodcenter-.org/pdf/Anti-SARS%20Peptide %20Model.pdf by Dr. Shibo Jiang.

The invention provides compositions and methods that are useful for preventing and treating a coronavirus infection in a subject. More specifically, the invention provides peptides and conjugates and pharmaceutical compositions containing those peptides and conjugates that block fusion of a coronavirus, such as the SARS virus, to a target cell. This blocking mechanism prevents or treats a coronavirus infection, such as a SARS infection, in a subject, such as a human subject.

SARS-CoV is a Novel Coronavirus

The sequence of the genome of the SARS-CoV was downloaded from the CDC website and translated into ten putative open reading frames (ORFs). The amino acid sequences corresponding to putative proteins encoded by the ten ORFs were analyzed for homology to existing proteins in the proteome using BLAST, a protein database searching program. See Altschul et al, *Nucleic Acids Res.* 25: 3389 (1997). A number of open reading frames were found to encode proteins with significant sequence homology to proteins from known coronaviruses. For example, ORF1 corresponds to a coronavirus polymerase protein (polymerase 1a, 1b), and ORF3 corresponds to a coronavirus spike protein (S). The homology and organization of the genome provide additional convincing evidence that the SARS virus is a coronavirus.

Coronaviruses previously have been grouped into three categories based on cross-reactivity of antibodies backed up by genetic data. The two previously identified human coronaviruses fall into two different groups. One of these groups includes a number of enteric coronoviruses that cause gastroenteritis. The other includes coronaviruses that cause respiratory or neurological diseases in diverse species. The third group includes coronaviruses isolated from avian species.

The sequence of the S protein from SARS-CoV shares about 30–35% identity throughout its 1260 or so amino acid length with S proteins from all three groups of coronaviruses, including coronaviruses from humans, cows, pigs, mice and chickens. Based on the sequence homology analysis, the SARS coronavirus represents the first, and so far only, member of a new fourth coronavirus group.

Spike Proteins are Required for Viral Entry

Numerous studies have shown that entry of enveloped viruses into host cells requires membrane fusion between virus and host cell. For most animal viruses, this fusion function is mediated by a single envelope glycoprotein on virions. The S protein has been shown to be the fusion protein that mediates cellular entry for coronavirus. See Spaan et al., *J. Gen. Virol.* 69:2939 (1988).

The S protein forms the peplomer projections that protrude from the virion surface as seen in electron micrographs. Peplomers are thought to be composed of three oligomerized S protein molecules. See Delmas et al., *J. Virol.* 64:5367 (1990).

The S protein is cleaved by host proteases during virus assembly into two similarly-sized subunits: S1 and S2. The C-terminal S2 subunit, which associates non-covalently with the N-terminal S1, anchors the S protein to the membrane through a transmembrane domain, while the S1 subunit contains the receptor binding activity of the S protein.

Helical Heptad Repeats in the S2 Subunit are Required for Fusion

Reviews of the roles of the coronavirus spike proteins in viral entry and pathogenesis can be found in Gallagher et al., *Virology* 279:371 (2001) and Luo et al, *J. Virol.* 73:8152 (1999). Several studies suggest that the S2 subunit is required for viral fusion. Functional mutagenesis studies indicate that critical residues for fusion are located within two regions in S2 that have been identified as heptad repeat regions. Helical heptad repeats are found in fusion proteins from other enveloped viruses, including paramyxoviruses, such as influenza virus, retroviruses, such as HIV, and filoviruses, such as Ebola virus. The existence of two heptad repeats, HR1 and HR2, separated by a non-helical spacer in the S2 subunit of coronaviruses is suggestive of the formation of a coiled-coil or "trimer of hairpins" fusogenic complex similar to the fusogenic structures thought to be formed by the helical heptad repeats in the fusion glycoproteins of, for example, HIV, influenza virus and Ebola virus.

In the case of HIV, a peptide sequence that mimics either HR1 or HR2 can prevent HIV fusion and block viral replication. Enfurvitide, a 38-residue peptide based on the sequence of HR2 of the HIV glycoprotein, is used clinically to treat HIV/AIDS. The present inventors reasoned that peptides that can bind to coiled-coil intermediates of coronaviruses should block the formation of a productive fusogenic complex and prevent virus entry (FIG. 1).

SARS-CoV Contains High Homology Regions with HR1 and HR2 of Coronaviruses that are Predicted to be Helical.

The amino acid sequence homology between the S protein of SARS-CoV and other coronaviruses was evaluated throughout its length. The highest homology resides in regions that overlap with the HR1 and HR2 heptad repeats in known coronoaviruses. Analysis of the S protein using secondary structure prediction methods (see for example program PROF as implemented on the CUBIST protein prediction server @http://cubic.bioc.columbia.edu) revealed that the HR1 and HR2 regions are strongly predicted to be helical (FIG. 2). The HR1 and HR2 regions were divided into five contiguous amino acids segments that are most strongly predicted to be helical. In the same fashion as observed with HIV gp41, heptad-containing sequences derived from the HR1 segments bind to HR2 helices. Similarly, heptad-containing sequences derived from the HR2 segments can bind to the HR1 helices. Peptides that bind to either HR1 or HR2 prevent virus entry, possibly by disrupting formation of the fusogenic complex. Such peptides, and compositions containing these peptides, are useful for treating infections caused by coronaviruses, and as prophylactics against coronavirus infection. These peptides are particularly useful for preventing and treating SARS infection.

The N peptides are predicted to form a trimeric coiled-coil with 3-fold symmetry similar to HR1 of HIV-gp41. The C peptides are predicted to form helices that bind in the grooves formed by adjacent N-helices in the coiled coil, similar to HR2 in HIV gp41. These peptide sequences are predicted to form continuous alpha helices constructed of series of contiguous, or nearly contiguous, helical heptad repeats in which the ith and i+4th residues are important or critical for oligomer formation.

The peptides contained in the S protein have the following sequences (most strongly predicted helical sequences are shown in bold)

C-terminal, HR2 peptide 1 (SEQ ID NO: 182) PDVDLGDISGINASVVNIQKEIDRLNE-VAKNLNESLIDLQELGKYEQYIK N-Terminal, HR1 peptide 2 (SEQ ID NO: 2) QIPFAM-QMAYRFNGIGVTQNVLYENQKQIANQFN-KAISQIQESLT N-Terminal, HR1 peptide 3 (SEQ ID NO: 3) ESLTTTS-TALGKLQDVVNQNAQALNTLVKQLSSNFGAISS N-Terminal, HR1 peptide 4 (SEQ ID NO: 4) GKLQDV-VNQNAQALNTLVKQLSSNFGAISSV-LNDILSRLDKVEAE N-Terminal, HR1 peptide 5 (SEQ ID NO: 183) QALNTLVKQLSSNFGAISSV-LNDILSRLDKVEAEVQIDRLITGRLQS N-Terminal, HR1 peptide 6 (SEQ ID NO: 5) RLITGR-LQSLQTYVTQQLIRAAEIRASANLAATK-MSECVLGQSKRVDF These sequences were used to design peptide inhibitors having between about 15 and about 50 amino acids, advantageously having 15 to 50 amino acids and containing at least 7 contiguous amino acids from one of the sequences shown above. Thus, for example, the peptides may contain one of the following 7 amino acid sequences:

for the C-terminal HR2 peptide 1 the peptide may contain one of the following sequences

| | |
|---|---|
| PDVDLGD | (SEQ ID NO:184) |
| DVDLGDI | (SEQ ID NO:185) |
| VDLGDIS | (SEQ ID NO:186) |
| DLGDISG | (SEQ ID NO:187) |
| LGDISGIN | (SEQ ID NO:188) |
| GDISGIN | (SEQ ID NO:189) |
| DISGINA | (SEQ ID NO:190) |
| ISGINAS | (SEQ ID NO:191) |
| SGINASV | (SEQ ID NO:192) |
| GINASVV | (SEQ ID NO:193) |
| INASVVN | (SEQ ID NO:194) |
| NASVVNI | (SEQ ID NO:195) |
| ASVVNIQ | (SEQ ID NO:196) |
| SVVNIQK | (SEQ ID NO:6) |
| VVNIQKE | (SEQ ID NO:7) |
| VNIQKEI | (SEQ ID NO:8) |
| NIQKEID | (SEQ ID NO:9) |
| IQKEIDR | (SEQ ID NO:10) |

-continued

| | |
|---|---|
| QKEIDRL | (SEQ ID NO:11) |
| KEIDRLN | (SEQ ID NO:12) |
| EIDRLNE | (SEQ ID NO:13) |
| IDRLNEV | (SEQ ID NO:14) |
| DRLNEVA | (SEQ ID NO:15) |
| RLNEVAK | (SEQ ID NO:16) |
| LNEVAKN | (SEQ ID NO:17) |
| NEVAKNL | (SEQ ID NO:18) |
| EVAKNLN | (SEQ ID NO:19) |
| VAKNLNE | (SEQ ID NO:20) |
| AKNLNES | (SEQ ID NO:21) |
| KNLNESL | (SEQ ID NO:22) |
| NLNESLI | (SEQ ID NO:23) |
| LNESLID | (SEQ 1ID NO:24) |
| NESLIDL | (SEQ ID NO:25) |
| ESLIDLQ | (SEQ ID NO:26) |
| SLIDLQE | (SEQ ID NO:27) |
| LIDLQEL | (SEQ ID NO:28) |
| IDLQELG | (SEQ ID NO:29) |
| DLQELGK | (SEQ ID NO:30) |
| LQELGKY | (SEQ ID NO:31) |
| QELGKYE | (SEQ ID NO:32) |
| ELGKYEQ | (SEQ ID NO:33) |
| LGKYEQY | (SEQ ID NO:34) |
| GKYEQYI | (SEQ ID NO:35) |
| KYEQYIK | (SEQ ID NO:36) | for the N-Terminal, HR1 peptide 2 the peptide may contain one of the following sequences

| | |
|---|---|
| QIPFAMQ | (SEQ ID NO:37) |
| IPFAMQM | (SEQ ID NO:38) |
| PFAMQMA | (SEQ ID NO:39) |
| FAMQMAY | (SEQ ID NO:40) |
| AMQMAYR | (SEQ ID NO:41) |
| MQMAYRF | (SEQ ID NO:42) |
| QMAYRFN | (SEQ ID NO:43) |
| MAYRFNG | (SEQ ID NO:44) |
| AYRFNGI | (SEQ ID NO:45) |
| YRFNGIG | (SEQ ID NO:46) |
| RFNGIGV | (SEQ ID NO:47) |
| FNGIGVT | (SEQ ID NO:48) |
| NGIGVTQ | (SEQ ID NO:49) |

-continued

| | |
|---|---|
| IGVTQNV | (SEQ ID NO:50) |
| GVTQNVL | (SEQ ID NO:51) |
| VTQNVLY | (SEQ ID NO:52) |
| TQNVLYE | (SEQ ID NO:53) |
| QNYLYEN | (SEQ ID NO:54) |
| NVLYENQ | (SEQ ID NO:55) |
| VLYENQK | (SEQ ID NO:56) |
| LYENQKQ | (SEQ ID NO:57) |
| YENQKQI | (SEQ ID NO:58) |
| ENQKQIA | (SEQ ID NO:59) |
| NQKQIAN | (SEQ ID NO:60) |
| QKQIANQ | (SEQ ID NO:61) |
| KQIANQF | (SEQ ID NO:62) |
| QIANQFN | (SEQ ID NO:63) |
| IANQFNK | (SEQ ID NO:64) |
| ANQFNKA | (SEQ ID NO:65) |
| NQFNKAI | (SEQ ID NO:66) |
| QFNKAIS | (SEQ ID NO:67) |
| FNKAISQ | (SEQ ID NO:68) |
| NKAISQI | (SEQ ID NO:69) |
| KAISQIQ | (SEQ ID NO:70) |
| AISQIQE | (SEQ ID NO:71) |
| ISQIQES | (SEQ ID NO:72) |
| SQIQESL | (SEQ ID NO:73) |
| QIQESLT | (SEQ ID NO:74) | for the N-Terminal, HR1 peptide 3, the peptide may contain one of the following sequences

| | |
|---|---|
| ESLTTTS | (SEQ ID NO:75) |
| SLTTTST | (SEQ ID NO:76) |
| LTTTSTA | (SEQ ID NO:77) |
| TTTSTAL | (SEQ ID NO:78) |
| TTSTALG | (SEQ ID NO:79) |
| TSTALGK | (SEQ ID NO:80) |
| STALGKL | (SEQ ID NO:81) |
| TALGKLQ | (SEQ ID NO:82) |
| ALGKLQD | (SEQ ID NO:83) |
| LGKLQDV | (SEQ ID NO:84) |
| GKLQDVV | (SEQ ID NO:85) |
| KLQDVVN | (SEQ ID NO:86) |
| LQDVVNQ | (SEQ ID NO:87) |
| QDVVNQN | (SEQ ID NO:88) |
| DVVNQNA | (SEQ ID NO:89) |
| VVNQNAQ | (SEQ ID NO:90) |
| VNQNAQA | (SEQ ID NO:91) |
| NQNAQAL | (SEQ ID NO:92) |
| QNAQALN | (SEQ ID NO:93) |
| NAQALNT | (SEQ ID NO:94) |
| AQALNTL | (SEQ ID NO:95) |
| QALNTLV | (SEQ ID NO:96) |
| ALNTLVK | (SEQ ID NO:97) |
| LNTLVKQ | (SEQ ID NO:98) |
| NTLVKQL | (SEQ ID NO:99) |
| TLVKQLS | (SEQ LB NO:100) |
| LVKQLSS | (SEQ ID NO:101) |
| VKQLSSN | (SEQ ID NO:102) |
| KQLSSNF | (SEQ ID NO:103) |
| QLSSNFG | (SEQ ID NO:104) |
| LSSNFGA | (SEQ ID NO:105) |
| SSNFGAI | (SEQ ID NO:106) |
| SNFGAIS | (SEQ ID NO:107) |
| NFGAISS | (SEQ ID NO:108) | for the N-Terminal, HR1 peptide 4, the peptide may contain one of the following sequences:

| | |
|---|---|
| LQDVVNQ | (SEQ ID NO:109) |
| QDVVNQN | (SEQ ID NO:110) |
| DVVNQNA | (SEQ ID NO:111) |
| VVNQNAQ | (SEQ ID NO:112) |
| VNQNAQA | (SEQ ID NO:113) |
| NQNAQAL | (SEQ ID NO:114) |
| QNAQALN | (SEQ ID NO:115) |
| NAQALNT | (SEQ ID NO:116) |
| AQALNTL | (SEQ ID NO:117) |
| QALNTLV | (SEQ ID NO:118) |
| ALNTLVK | (SEQ ID NO:119) |
| LNTLVKQ | (SEQ ID NO:120) |
| NTLVKQL | (SEQ ID NO:121) |
| TLVKQLS | (SEQ ID NO:122) |
| LVKQLSS | (SEQ ID NO:123) |
| VKQLSSN | (SEQ ID NO:124) |
| KQLSSNF | (SEQ ID NO:125) |
| QLSSNFG | (SEQ ID NO:126) |
| LSSNFGA | (SEQ ID NO:127) |

-continued

| | |
|---|---|
| SSNFGAI | (SEQ ID NO:128) |
| SNFGAIS | (SEQ ID NO:129) |
| NEGAISS | (SEQ ID NO:130) |
| FGAISSV | (SEQ ID NO:131) |
| GAISSVL | (SEQ ID NO:132) |
| AISSVLN | (SEQ ID NO:133) |
| ISSVLND | (SEQ ID NO:134) |
| SSVLNDI | (SEQ ID NO:135) |
| SVLNDIL | (SEQ ID NO:136) |
| VLNDILS | (SEQ ID NO:137) |
| LNDILSR | (SEQ ID NO:138) |
| NDILSRL | (SEQ ID NO:139) |
| DILSRLD | (SEQ ID NO:140) |
| ILSRLDK | (SEQ ID NO:141) |
| LSRLDK | (SEQ ID NO:142) |
| SRLDKV | (SEQ ID NO:143) |
| RLDKVE | (SEQ ID NO:144) |
| LDKVEA, | (SEQ ID NO:145) | and for the N-Terminal, HR1 peptide 5 the peptide may contain one of the following sequences:

| | |
|---|---|
| RLITGRL | (SEQ ID NO:146) |
| LITGRLQ | (SEQ ID NO:147) |
| ITGRLQS | (SEQ ID NO:148) |
| TGRLQSL | (SEQ ID NO:149) |
| GRLQSLQ | (SEQ ID NO:150) |
| RLQSLQT | (SEQ ID NO:151) |
| LQSLQTY | (SEQ ID NO:152) |
| QSLQTYV | (SEQ ID NO:153) |
| SLQTYVT | (SEQ ID NO:154) |
| LQTYVTQ | (SEQ ID NO:155) |
| QTYVTQQ | (SEQ ID NO:156) |
| TYVTQQL | (SEQ ID NO:157) |
| YVTQQLI | (SEQ ID NO:158) |
| VTQQLIR | (SEQ ID NO:159) |
| TQQLIRA | (SEQ ID NO:160) |
| QQLIRAA | (SEQ ID NO:161) |
| QLIRAAE | (SEQ ID NO:162) |
| LIRAAEI | (SEQ ID NO:163) |
| IRAAEIR | (SEQ ID NO:164) |
| RAAEIRA | (SEQ ID NO:165) |
| AAEIRAS | (SEQ ID NO:166) |

-continued

| | |
|---|---|
| AFIRASA | (SEQ ID NO:167) |
| EIRASAN | (SEQ ID NO:168) |
| IRASANL | (SEQ ID NO:169) |
| RASANLA | (SEQ ID NO:170) |
| ASANLAA | (SEQ ID NO:171) |
| SANLAAT | (SEQ ID NO:172) |
| ANLAATK | (SEQ ID NO:173) |
| NLAATKM | (SEQ ID NO:174) |
| LAATKMS | (SEQ ID NO:175) |
| AATKMSE | (SEQ ID NO:176) |
| ATKMSEC | (SEQ ID NO:177) |
| TKMSECV | (SEQ ID NO:178) |
| KMSECVL | (SEQ ID NO:179) |
| MSECVLG | (SEQ ID NO:180) |

Moreover, because only certain of the amino acids of the peptide make contact in the grooves formed by adjacent N-helices in the coiled coil, amino acids at non-groove binding positions can be replaced with essentially any other amino acid to make "mutated" peptide inhibitors. In addition, amino acids at positions that make groove contact also may be replaced with certain preferred amino acids. Thus, in the peptide

DVDLGDISGINASVVNIQKEIDRLNE-VAKNLNESLIDLQELGKYEQYIK; (SEQ ID NO: 1)

the amino acids at bold letter positions can be substituted with an amino acid selected from the group consisting of I, L, V, W, Y, F, N, Q, S, T, D, E, G, H, and M. Of these amino acids, I, L, V, W, and Y are most preferred, and F, N, Q, S, and T are next most preferred, although D, E, G, H, and M also may be used. The amino acids in non-bold positions can be any amino acid except proline, which is predicted to break the helical structure and therefore prevent groove binding. As with the above peptide, a peptide containing any seven contiguous residues of such a mutated peptide can be used.

These peptide sequences are contained within a longer peptide sequence containing at least 15 and up to 50 amino acids. The additional amino acids may be at the N and/or C termini of the sequences shown.

The peptide inhibitors may also contain at least 10, 15, 20, 25, 30, 35, or 40 contiguous amino acids from one of the sequences shown above, while remaining within the length limitations described above. The peptides may also be linked to carriers, such as carrier proteins, described in more detail below, in which case the entire molecule may contain more than 50 amino acids, but the portion of the molecule responsible for cell binding will still contain up to 50 amino acids.

The peptide of the invention may have the following general structure:

B—X—Z, where B is an amino acid sequence containing up to about 43 amino acids, or B is an amino group, an acetyl group, a 9-fluorenylmethoxy-carbonyl group, a hydrophobic group, or a macromolecule carrier group. B also may comprise a carrier protein, such as HSA, in which case B may contain more than 8 amino acids, and may also comprises a linker peptide sequence that connects the antiviral sequence to the carrier protein.

Z is an amino acid sequence containing up to about 43 amino acids, or Z comprises a carboxyl group, an amido group, a hydrophobic group, or a macromolecular carrier group. Z also may comprise a carrier protein, such as HSA, in which case Z may contain more than 8 amino acids, and may also comprise a linker peptide sequence that connects the antiviral sequence to the carrier protein. The peptide and the carrier may also be linked as a chemical conjugate, via a linker such as a maleimide linker of the type that is commercially available from, for example, Pierce (Rockford, Ill.).

When considered together B and Z must contain at least 8 amino acids between the B and Z groups. Typically, only one of B and Z is a macromolecule or carrier protein X is any 7, 10, 15, 20, 25, 30, 35, or 40 contiguous amino acids from the C or N peptides identified above.

The peptides of the invention also may comprise peptide sequences that exhibit 70% or more sequence identity with at least 7 10, 15, 20, 25, 30, 35, or 40 contiguous amino acids from one of the sequences shown above, while remaining within the length limitations described above.

The peptides of the invention also may comprise peptide sequences that exhibit identity in any two of the seven positions of the contiguous heptapeptide peptides described above, while remaining within the length limitations described above. This sequence identity advantageously may be located in the ith and i+4th positions in the contiguous heptapeptide peptides described above.

Ex vivo conjugation of the peptides of the invention moiety to a macromolecule such as HSA produces a highly soluble conjugate that can be purified and administered in tightly controlled dosage. The cloaked conjugate is biologically active as the conjugate, i.e. it does not act as a prodrug that releases the peptide moiety from the conjugate and cleavage of the conjugate is not required for biological activity. Moreover, once administered to a subject the conjugate has a surprisingly long in vivo half-life, has excellent tissue distribution and produces sustained activity corresponding to the activity of the biologically active moiety of the conjugate.

Advantageously, the peptide and the carrier protein and the macromolecule are linked in an approximately 1:1 ratio, to avoid "haptenization" of the biologically active moiety and generation of an immune response to the conjugate. Moreover, the peptide is advantageously appended to a single site in the macromolecule. For example, selective linkage to the unusually reactive cysteine 34 (C34) of HSA may be used. Methods for selective linkage to C34 using, for example, a maleimide containing linker, are known in the art.

In the event that more than one molecule of peptide is linked to the macromolecule, this is advantageously achieved via a "multivalent" linker that is attached to a single point of the macromolecule. For example, a linker can be appended to C34 of HSA that permits attachment of a plurality of peptides to the linker. Multivalent linkers are known in the art and can contain, for example, a thiophilic group for reaction with C34 of HSA, and multiple nucleophilic (such as NH or OH) or electrophilic (such as activated ester) groups that permit attachment of a plurality of peptides to the linker.

Preparation of Peptides of the Invention

The peptides of the invention may be synthesized or prepared by techniques well known in the art. Peptide synthesizers are commercially available from, for example, Applied Biosystems or Milligen/Biosearch. See also, for example, Creighton, 1983, Proteins: Structures and Molecular Principles, W. H. Freeman and Co., N.Y., which is incorporated herein by reference in its entirety. Short peptides, for example, can be synthesized on a solid support or in solution. Longer peptides, or fusions of longer peptides with carrier proteins such as human serum albumin, may be made using recombinant DNA techniques. Nucleotide sequences encoding the desired peptides or fusion proteins containing the peptides may be synthesized, and/or cloned, and expressed according to techniques well known to those of ordinary skill in the art. See, for example, Sambrook, et al., 1989, Molecular Cloning, A Laboratory Manual, Vols. 1–3, Cold Spring Harbor Press, N.Y.

The peptides also may be synthesized such that one or more of the bonds linking the amino acid residues of the peptides are non-peptide bonds. Alternative non-peptide bonds may be formed by reactions well known to those in the art, and may include, but are not limited to imino, ester, hydrazide, semicarbazide, and azo bonds. In yet another embodiment of the invention, peptides comprising the sequences described above may be synthesized with additional chemical groups present at their amino and/or carboxy termini, such that, for example, the stability, bioavailability, and/or inhibitory activity of the peptides is enhanced. For example, hydrophobic groups such as carbobenzoxyl, dansyl, or t-butyloxycarbonyl groups, may be added to a peptide's amino terminus. Likewise, an acetyl group or a 9-fluorenylmethoxy-carbonyl group may be placed at a peptide's amino terminus. Additionally, a hydrophobic group, t-butyloxycarbonyl, or an amido group may be added to a peptide's carboxy terminus. Further, non-naturally occurring amino acids can be used to improve a peptide's stability, bioavailability, or binding/inhibitory characteristics. For example, methionine can be replaced with norleucine. Other non-naturally occurring amino acid residues are well known.

The peptides of the invention also may contain amino acid substitutions, which may be of a conserved or non-conserved nature. Conserved amino acid substitutions consist of replacing one or more amino acids in a peptide sequence with amino acids of similar charge, size, and/or hydrophobicity characteristics, such as, for example, a glutamic acid (E) to aspartic acid (D) amino acid substitution. When only conserved substitutions are made, the resulting peptide retains the functionality of the unsubstituted peptide. Non-conserved substitutions consist of replacing one or more amino acids of a peptide sequence with amino acids possessing dissimilar charge, size, and/or hydrophobicity characteristics, such as, for example, a glutamic acid (E) to valine (V) substitution. The peptides of the present invention may advantageously contain amino acid substitutions of a conserved nature.

The stability of the peptides of the invention may be increased by either in vivo or ex vivo linkage to a carrier protein, such as a blood component. Suitable blood components for use in the present invention are known in the art. Human serum albumin ("HSA") is a predominant component of human blood and is particularly suited for use in the present invention. In particular, HSA has an exposed surface cysteine residue that provides a reactive thiol moiety for covalent linkage of the peptides compounds to the protein. Activated linkers that are particularly suited for linkage to thiols include unsaturated cyclic imides such as maleimides, α-halo esters, such as α-iodo- and α-bromo acetates, and vinyl pyridine derivative. Such linkers can be added to the peptides during synthesis and can be added at any point in the sequence although the N and/or C terminus advantageously is used. Suitable activated linkers are commercially available from, for example, Pierce Chemical (Rockford, Ill.). Methods for preparing suitable activated compounds for linking to HSA are known in art. See for example, U.S. Pat. No. 5,612,034, which is incorporated herein in its entirety.

Moreover, the gene for HSA has been cloned, which permits the ready preparation of fusion proteins of the peptides and HSA. Methods of making fusion proteins are known in the art. See, for example, WO01/79271 and WO01/79258, the contents of which are hereby incorporated by reference in their entirety. The preparation of fusion proteins is useful for preparing persistent derivatives of the present anti-viral peptides.

Another blood component that is suitable for linkage to the anti-viral compounds is an immunoglobulin ("Ig") molecule. Igs are persistent and are present in relatively high concentration in the blood. For in vitro coupling, Igs have the advantage of being readily stable and readily isolated, and methods of making Ig conjugates are well known in the art. Moreover, Ig genes may readily be cloned and recombinant Ig and Ig fusion proteins prepared. Methods for obtaining fully human Igs are well known in the art. See for example, U.S. Pat. Nos. 5,969,108 and 6,300,064, the contents of which are hereby incorporated by reference in their entirety. In addition, phage display methods for selecting Igs having a particularly desired binding activity, for example, for binding to HSA, are well known in the art. See U.S. Pat. Nos. 5,885,793, 5,969,108 and 6,300,064. In the context of the present invention, an Ig refers to any suitable immunoglobulin or immunogolobulin derivative known in the art, and includes, for example, whole IgG, IgM, Fab fragments, F(ab')2 fragments, and single chain Fv fragments.

Other blood components suitable for use in the present invention include transferrin, ferritin, steroid binding proteins, thyroxin binding protein, and α-2-macroglobulin.

In the peptides, the activated linkers also may be coupled to reactive side chain residues, such as lysine side chains. For example, a linker containing an active ester moiety and a maleimide moiety can be selectively reacted at the active ester (such as an N-hydroxysuccinimidyl ester) via lysine side chains or at the N-terminus of the peptide.

Both natural and recombinant HSA and human Igs are commercially available and are suitable for use in the present invention.

The peptides also may have a non-peptide macromolecular carrier group covalently attached to their amino and/or carboxy termini. Such macromolecular carrier groups may include, for example, lipid-fatty acid conjugates, polyethylene glycol, or carbohydrates.

Use of the Peptides

The peptides of the invention exhibit potent antiviral activity against coronaviruses, such as for example, the SARS virus. As such, the peptides may be used as inhibitors of human and non-human coronoviruses, especially SARS, transmission to uninfected cells. Various peptides from the C-terminal HR2 domains of S2 proteins of SARS virus and murine hepatitis virus (MHV) have been shown to exhibit antiviral activity against these viruses in cell culture assays (see for example Liu et al., Lancet 363: 938 (2004); and Bosch et al., J. Virol. 77:8801 (2003). The human SARS viruses whose transmission may be inhibited by the peptides of the invention include, but are not limited to all strains of the SARS virus. The non-human retroviruses whose transmission may be inhibited by the peptides of the invention include, but are not limited to coronaviruses that infect domestic animals and livestock, for example, coronaviruses from cows, pigs, mice-and chickens. However, as will be appreciated by one skilled in the art, the peptides used for preventing coronaviruses will be most effective when derived using the specific sequence of the infecting virus strain.

With respect to SARS in humans, the peptides of the invention may be used as a therapeutic in the treatment of SARS infections. The peptides of the invention may be administered using techniques well known to those in the art. Preferably, agents are formulated and administered systemically. Techniques for formulation and administration may be found in "Remington's Pharmaceutical Sciences" 18th ed., 1990 Mack Publishing Co., Easton, Pa. Suitable routes may include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few. Most preferably, administration is intravenous. For injection, the agents of the invention may be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art. Other diluents, adjuvants, and excipients are known in the art.

In addition, the peptides may be used as a prophylactic measure in previously uninfected individuals after acute exposure to a SARS virus. Examples of such prophylactic use of the peptides may include, but are not limited to, settings where the likelihood of SARS transmission exists, such as, for example, in hospitals and transport termini such as airports and train stations. The peptides of the invention in such cases may serve the role of a prophylactic vaccine, wherein the host raises antibodies against the peptides of the invention, which then serve to neutralize SARS viruses by, for example, inhibiting further SARS infection. Administration of the peptides of the invention as a prophylactic vaccine, therefore, would comprise administering to a host a concentration of peptides effective in raising an immune response which is sufficient to neutralize SARS or a related coronavirus, by, for example, inhibiting SARS ability to infect cells. The exact concentration will depend upon the specific peptide to be administered, but may be determined by using standard techniques for assaying the development of an immune response which are well known to those of ordinary skill in the art. The peptides to be used as vaccines are usually administered intramuscularly.

The peptides may be formulated with a suitable adjuvant in order to enhance the immunological response. Such adjuvants may include, but are not limited to mineral gels such as aluminum hydroxide; surface active substances such as lysolecithin, pluronic polyols, polyanions; other peptides; oil emulsions; and potentially useful human adjuvants such as BCG and Corynebacterium parvum. Many methods may be used to introduce the vaccine formulations described here. These methods include but are not limited to oral, intradermal, intramuscular, intraperitoneal, intravenous, subcutaneous, and intranasal routes.

Alternatively, an effective concentration of polyclonal or monoclonal antibodies raised against the peptides of the invention may be administered to a host so that no uninfected cells become infected by the SARS virus or other coronavirus. The exact concentration of such antibodies will vary according to each specific antibody preparation, but may be determined using standard techniques well known to those of ordinary skill in the art. Administration of the antibodies may be accomplished using a variety of techniques, including, but not limited to those described in this section.

Effective dosages of the peptides of the invention to be administered may be determined through procedures well known to those in the art which address such parameters as biological half-life, bioavailability, and toxicity.

The antiviral activity of the peptides of the invention may show a pronounced type and subtype specificity, i.e., specific peptides may be effective in inhibiting the activity of only specific coronaviruses. This feature of the invention presents many advantages. One such advantage, for example, lies in the field of diagnostics, wherein one can use the antiviral specificity of the peptide of the invention to ascertain the identity of a viral isolate. With respect to coronaviruses, one may easily determine whether a viral isolate consists of a coronavirus that causes SARS or a virus that causes milder cold-like symptoms. For example, uninfected cells may be co-infected with a coronavirus isolate which has been identified as containing a SARS virus. A peptide of the invention may be added which is known to be active against the SARS virus, after which the retroviral activity of cell supernatants may be assayed, using known methods. Those isolates whose viral activity is completely or nearly completely inhibited contain the SARS virus. Those isolates whose viral activity is unchanged or only reduced by a small amount, may be considered to not contain the SARS virus. Such an isolate may then be treated with one or more of the other peptides of the invention, and subsequently be tested for its viral activity in order to determine the identify of the viral isolate.

What is claimed is:

1. An antiviral molecule, wherein said molecule exhibits antiviral activity against a coronavirus, wherein said molecule comprises a peptide linked to human serum albumin, and wherein said peptide contains up to 40 amino acids and comprises the sequence:

VVNIQKEIDRLNEVAKNLNESLIDLQELGKYEQYIK (SEQ ID NO: 181).

2. A pharmaceutical composition comprising a molecule according to claim 1 and a pharmaceutically acceptable diluent, adjuvant and/or excipient.

3. A method of treating or a SARS infection in a subject, comprising administering to a patient suspected of suffering from said infection an effective amount of a composition according to claim 2.

4. The method according to claim 3, wherein said subject is a human.

5. An antiviral molecule, wherein said molecule exhibits antiviral activity against a coronavirus, wherein said molecule comprises a peptide linked to human serum albumin, and wherein said peptide consists of the sequence:

VVNIQKEIDRLNEVAKNLNESLIDLQELGKYEQYIK (SEQ ID NO: 181).

6. A pharmaceutical composition comprising a molecule according to claim 5 and a pharmaceutically acceptable diluent, adjuvant and/or excipient.

7. A method of treating a SARS infection in a subject, comprising administering to a patient suspected of suffering from said infection an effective amount of a composition according to claim 6.

8. The method according to claim 7, wherein said subject is a human.

* * * * *

SEQUENCE LISTING

<160> NUMBER OF SEQ ID NOS: 197

<210> SEQ ID NO 1
<211> LENGTH: 49
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asp Val Asp Leu Gly Asp Ile Ser Gly Ile Asn Ala Ser Val Val Asn
1               5                   10                  15

Ile Gln Lys Glu Ile Asp Arg Leu Asn Glu Val Ala Lys Asn Leu Asn
            20                  25                  30

Glu Ser Leu Ile Asp Leu Gln Glu Leu Gly Lys Tyr Glu Gln Tyr Ile
        35                  40                  45

Lys

<210> SEQ ID NO 2
<211> LENGTH: 45
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gln Ile Pro Phe Ala Met Gln Met Ala Tyr Arg Phe Asn Gly Ile Gly
1               5                   10                  15

Val Thr Gln Asn Val Leu Tyr Glu Asn Gln Lys Gln Ile Ala Asn Gln
            20                  25                  30

Phe Asn Lys Ala Ile Ser Gln Ile Gln Glu Ser Leu Thr
        35                  40                  45

<210> SEQ ID NO 3
<211> LENGTH: 40
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 3

Glu Ser Leu Thr Thr Thr Ser Thr Ala Leu Gly Lys Leu Gln Asp Val
1               5                   10                  15

Val Asn Gln Asn Ala Gln Ala Leu Asn Thr Leu Val Lys Gln Leu Ser
            20                  25                  30

Ser Asn Phe Gly Ala Ile Ser Ser
        35                  40

<210> SEQ ID NO 4
<211> LENGTH: 45
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Lys Leu Gln Asp Val Val Asn Gln Asn Ala Gln Ala Leu Asn Thr
1               5                   10                  15

Leu Val Lys Gln Leu Ser Ser Asn Phe Gly Ala Ile Ser Ser Val Leu
            20                  25                  30

Asn Asp Ile Leu Ser Arg Leu Asp Lys Val Glu Ala Glu
        35                  40                  45

<210> SEQ ID NO 5
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Leu Ile Thr Gly Arg Leu Gln Ser Leu Gln Thr Tyr Val Thr Gln
1               5                   10                  15

Gln Leu Ile Arg Ala Ala Glu Ile Arg Ala Ser Ala Asn Leu Ala Ala
            20                  25                  30

Thr Lys Met Ser Glu Cys Val Leu Gly Gln Ser Lys Arg Val Asp Phe
        35                  40                  45

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Val Val Asn Ile Gln Lys
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Val Val Asn Ile Gln Lys Glu

```
1               5
```

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

```
Val Asn Ile Gln Lys Glu Ile
1               5
```

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

```
Asn Ile Gln Lys Glu Ile Asp
1               5
```

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

```
Ile Gln Lys Glu Ile Asp Arg
1               5
```

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

```
Gln Lys Glu Ile Asp Arg Leu
1               5
```

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

```
Lys Glu Ile Asp Arg Leu Asn
1               5
```

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic

```
                          peptide

<400> SEQUENCE: 13

Glu Ile Asp Arg Leu Asn Glu
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ile Asp Arg Leu Asn Glu Val
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Arg Leu Asn Glu Val Ala
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Leu Asn Glu Val Ala Lys
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Asn Glu Val Ala Lys Asn
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asn Glu Val Ala Lys Asn Leu
1               5

<210> SEQ ID NO 19
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Glu Val Ala Lys Asn Leu Asn
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Val Ala Lys Asn Leu Asn Glu
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Lys Asn Leu Asn Glu Ser
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Lys Asn Leu Asn Glu Ser Leu
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asn Leu Asn Glu Ser Leu Ile
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24
```

```
Leu Asn Glu Ser Leu Ile Asp
1               5
```

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

```
Asn Glu Ser Leu Ile Asp Leu
1               5
```

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

```
Glu Ser Leu Ile Asp Leu Gln
1               5
```

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

```
Ser Leu Ile Asp Leu Gln Glu
1               5
```

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Leu Ile Asp Leu Gln Glu Leu
1               5
```

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

```
Ile Asp Leu Gln Glu Leu Gly
1               5
```

<210> SEQ ID NO 30
<211> LENGTH: 7
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 30

Asp Leu Gln Glu Leu Gly Lys
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Leu Gln Glu Leu Gly Lys Tyr
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Glu Leu Gly Lys Tyr Glu
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Glu Leu Gly Lys Tyr Glu Gln
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Leu Gly Lys Tyr Glu Gln Tyr
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Lys Tyr Glu Gln Tyr Ile
1               5

```
<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Lys Tyr Glu Gln Tyr Ile Lys
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gln Ile Pro Phe Ala Met Gln
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ile Pro Phe Ala Met Gln Met
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Pro Phe Ala Met Gln Met Ala
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Phe Ala Met Gln Met Ala Tyr
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41
```

Ala Met Gln Met Ala Tyr Arg
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Met Gln Met Ala Tyr Arg Phe
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gln Met Ala Tyr Arg Phe Asn
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Met Ala Tyr Arg Phe Asn Gly
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Tyr Arg Phe Asn Gly Ile
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Tyr Arg Phe Asn Gly Ile Gly
1               5

<210> SEQ ID NO 47
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 47

Arg Phe Asn Gly Ile Gly Val
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Phe Asn Gly Ile Gly Val Thr
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Asn Gly Ile Gly Val Thr Gln
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ile Gly Val Thr Gln Asn Val
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Val Thr Gln Asn Val Leu
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Val Thr Gln Asn Val Leu Tyr
1               5
```

```
<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Thr Gln Asn Val Leu Tyr Glu
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gln Asn Val Leu Tyr Glu Asn
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asn Val Leu Tyr Glu Asn Gln
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Val Leu Tyr Glu Asn Gln Lys
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Leu Tyr Glu Asn Gln Lys Gln
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 58

Tyr Glu Asn Gln Lys Gln Ile
1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Glu Asn Gln Lys Gln Ile Ala
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Asn Gln Lys Gln Ile Ala Asn
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gln Lys Gln Ile Ala Asn Gln
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Lys Gln Ile Ala Asn Gln Phe
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Ile Ala Asn Gln Phe Asn
1               5

<210> SEQ ID NO 64
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 64

Ile Ala Asn Gln Phe Asn Lys
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Asn Gln Phe Asn Lys Ala
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Asn Gln Phe Asn Lys Ala Ile
1               5

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gln Phe Asn Lys Ala Ile Ser
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Phe Asn Lys Ala Ile Ser Gln
1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asn Lys Ala Ile Ser Gln Ile
1               5
```

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Lys Ala Ile Ser Gln Ile Gln
1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ala Ile Ser Gln Ile Gln Glu
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ile Ser Gln Ile Gln Glu Ser
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ser Gln Ile Gln Glu Ser Leu
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Ile Gln Glu Ser Leu Thr
1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 75

Glu Ser Leu Thr Thr Thr Ser
1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ser Leu Thr Thr Thr Ser Thr
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Leu Thr Thr Thr Ser Thr Ala
1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Thr Thr Thr Ser Thr Ala Leu
1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Thr Thr Ser Thr Ala Leu Gly
1               5

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Thr Ser Thr Ala Leu Gly Lys
1               5

<210> SEQ ID NO 81
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ser Thr Ala Leu Gly Lys Leu
1               5

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Thr Ala Leu Gly Lys Leu Gln
1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ala Leu Gly Lys Leu Gln Asp
1               5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Leu Gly Lys Leu Gln Asp Val
1               5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Lys Leu Gln Asp Val Val
1               5

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Lys Leu Gln Asp Val Val Asn
```

```
<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Leu Gln Asp Val Val Asn Gln
1               5

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gln Asp Val Val Asn Gln Asn
1               5

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Asp Val Val Asn Gln Asn Ala
1               5

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Val Val Asn Gln Asn Ala Gln
1               5

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Val Asn Gln Asn Ala Gln Ala
1               5

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 92

Asn Gln Asn Ala Gln Ala Leu
1               5

<210> SEQ ID NO 93
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gln Asn Ala Gln Ala Leu Asn
1               5

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Asn Ala Gln Ala Leu Asn Thr
1               5

<210> SEQ ID NO 95
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ala Gln Ala Leu Asn Thr Leu
1               5

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gln Ala Leu Asn Thr Leu Val
1               5

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ala Leu Asn Thr Leu Val Lys
1               5

<210> SEQ ID NO 98

<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Leu Asn Thr Leu Val Lys Gln
1               5

<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Asn Thr Leu Val Lys Gln Leu
1               5

<210> SEQ ID NO 100
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Thr Leu Val Lys Gln Leu Ser
1               5

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Leu Val Lys Gln Leu Ser Ser
1               5

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Val Lys Gln Leu Ser Ser Asn
1               5

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

```
Lys Gln Leu Ser Ser Asn Phe
1               5

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gln Leu Ser Ser Asn Phe Gly
1               5

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Leu Ser Ser Asn Phe Gly Ala
1               5

<210> SEQ ID NO 106
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ser Ser Asn Phe Gly Ala Ile
1               5

<210> SEQ ID NO 107
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ser Asn Phe Gly Ala Ile Ser
1               5

<210> SEQ ID NO 108
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Asn Phe Gly Ala Ile Ser Ser
1               5

<210> SEQ ID NO 109
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 109

Leu Gln Asp Val Val Asn Gln
1               5

<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gln Asp Val Val Asn Gln Asn
1               5

<210> SEQ ID NO 111
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Asp Val Val Asn Gln Asn Ala
1               5

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Val Val Asn Gln Asn Ala Gln
1               5

<210> SEQ ID NO 113
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Val Asn Gln Asn Ala Gln Ala
1               5

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Asn Gln Asn Ala Gln Ala Leu
1               5
```

```
<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gln Asn Ala Gln Ala Leu Asn
1               5

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Asn Ala Gln Ala Leu Asn Thr
1               5

<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Ala Gln Ala Leu Asn Thr Leu
1               5

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gln Ala Leu Asn Thr Leu Val
1               5

<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ala Leu Asn Thr Leu Val Lys
1               5

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120
```

Leu Asn Thr Leu Val Lys Gln
1               5

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Asn Thr Leu Val Lys Gln Leu
1               5

<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Thr Leu Val Lys Gln Leu Ser
1               5

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Leu Val Lys Gln Leu Ser Ser
1               5

<210> SEQ ID NO 124
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Val Lys Gln Leu Ser Ser Asn
1               5

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Lys Gln Leu Ser Ser Asn Phe
1               5

<210> SEQ ID NO 126
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 126

Gln Leu Ser Ser Asn Phe Gly
1               5

<210> SEQ ID NO 127
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Leu Ser Ser Asn Phe Gly Ala
1               5

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ser Ser Asn Phe Gly Ala Ile
1               5

<210> SEQ ID NO 129
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ser Asn Phe Gly Ala Ile Ser
1               5

<210> SEQ ID NO 130
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Asn Phe Gly Ala Ile Ser Ser
1               5

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Phe Gly Ala Ile Ser Ser Val
1               5
```

<210> SEQ ID NO 132
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gly Ala Ile Ser Ser Val Leu
1               5

<210> SEQ ID NO 133
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ala Ile Ser Ser Val Leu Asn
1               5

<210> SEQ ID NO 134
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Ile Ser Ser Val Leu Asn Asp
1               5

<210> SEQ ID NO 135
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Ser Ser Val Leu Asn Asp Ile
1               5

<210> SEQ ID NO 136
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Ser Val Leu Asn Asp Ile Leu
1               5

<210> SEQ ID NO 137
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 137

Val Leu Asn Asp Ile Leu Ser
1               5

<210> SEQ ID NO 138
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Leu Asn Asp Ile Leu Ser Arg
1               5

<210> SEQ ID NO 139
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Asn Asp Ile Leu Ser Arg Leu
1               5

<210> SEQ ID NO 140
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Asp Ile Leu Ser Arg Leu Asp
1               5

<210> SEQ ID NO 141
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Ile Leu Ser Arg Leu Asp Lys
1               5

<210> SEQ ID NO 142
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Leu Ser Arg Leu Asp Lys
1               5

<210> SEQ ID NO 143
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 143

Ser Arg Leu Asp Lys Val
1               5

<210> SEQ ID NO 144
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Arg Leu Asp Lys Val Glu
1               5

<210> SEQ ID NO 145
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Leu Asp Lys Val Glu Ala
1               5

<210> SEQ ID NO 146
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Arg Leu Ile Thr Gly Arg Leu
1               5

<210> SEQ ID NO 147
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Leu Ile Thr Gly Arg Leu Gln
1               5

<210> SEQ ID NO 148
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ile Thr Gly Arg Leu Gln Ser
1               5
```

<210> SEQ ID NO 149
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Thr Gly Arg Leu Gln Ser Leu
1               5

<210> SEQ ID NO 150
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Gly Arg Leu Gln Ser Leu Gln
1               5

<210> SEQ ID NO 151
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Arg Leu Gln Ser Leu Gln Thr
1               5

<210> SEQ ID NO 152
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Leu Gln Ser Leu Gln Thr Tyr
1               5

<210> SEQ ID NO 153
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Gln Ser Leu Gln Thr Tyr Val
1               5

<210> SEQ ID NO 154
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 154

Ser Leu Gln Thr Tyr Val Thr
1               5

<210> SEQ ID NO 155
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Leu Gln Thr Tyr Val Thr Gln
1               5

<210> SEQ ID NO 156
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Gln Thr Tyr Val Thr Gln Gln
1               5

<210> SEQ ID NO 157
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Thr Tyr Val Thr Gln Gln Leu
1               5

<210> SEQ ID NO 158
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Tyr Val Thr Gln Gln Leu Ile
1               5

<210> SEQ ID NO 159
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Val Thr Gln Gln Leu Ile Arg
1               5

<210> SEQ ID NO 160
<211> LENGTH: 7
```

```
-continued

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Thr Gln Gln Leu Ile Arg Ala
1               5

<210> SEQ ID NO 161
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Gln Gln Leu Ile Arg Ala Ala
1               5

<210> SEQ ID NO 162
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Gln Leu Ile Arg Ala Ala Glu
1               5

<210> SEQ ID NO 163
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Leu Ile Arg Ala Ala Glu Ile
1               5

<210> SEQ ID NO 164
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Ile Arg Ala Ala Glu Ile Arg
1               5

<210> SEQ ID NO 165
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Arg Ala Ala Glu Ile Arg Ala
```

```
1               5
```

<210> SEQ ID NO 166
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

```
Ala Ala Glu Ile Arg Ala Ser
1               5
```

<210> SEQ ID NO 167
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

```
Ala Glu Ile Arg Ala Ser Ala
1               5
```

<210> SEQ ID NO 168
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

```
Glu Ile Arg Ala Ser Ala Asn
1               5
```

<210> SEQ ID NO 169
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

```
Ile Arg Ala Ser Ala Asn Leu
1               5
```

<210> SEQ ID NO 170
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

```
Arg Ala Ser Ala Asn Leu Ala
1               5
```

<210> SEQ ID NO 171
<211> LENGTH: 7
<212> TYPE: PRT
<213> ORGANISM: Artificial Sequence
<220> FEATURE:
<223> OTHER INFORMATION: Description of Artificial Sequence: Synthetic

```
                                    peptide

<400> SEQUENCE: 171

Ala Ser Ala Asn Leu Ala Ala
1               5

<210> SEQ ID NO 172
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Ser Ala Asn Leu Ala Ala Thr
1               5

<210> SEQ ID NO 173
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Ala Asn Leu Ala Ala Thr Lys
1               5

<210> SEQ ID NO 174
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Asn Leu Ala Ala Thr Lys Met
1               5

<210> SEQ ID NO 175
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Leu Ala Ala Thr Lys Met Ser
1               5

<210> SEQ ID NO 176
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Ala Ala Thr Lys Met Ser Glu
1               5

<210> SEQ ID NO 177
```

-continued

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Ala Thr Lys Met Ser Glu Cys
1               5

<210> SEQ ID NO 178
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Thr Lys Met Ser Glu Cys Val
1               5

<210> SEQ ID NO 179
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Lys Met Ser Glu Cys Val Leu
1               5

<210> SEQ ID NO 180
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Met Ser Glu Cys Val Leu Gly
1               5

<210> SEQ ID NO 181
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Val Val Asn Ile Gln Lys Glu Ile Asp Arg Leu Asn Glu Val Ala Lys
1               5                   10                  15

Asn Leu Asn Glu Ser Leu Ile Asp Leu Gln Glu Leu Gly Lys Tyr Glu
            20                  25                  30

Gln Tyr Ile Lys
        35

<210> SEQ ID NO 182
<211> LENGTH: 50
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 182

Pro Asp Val Asp Leu Gly Asp Ile Ser Gly Ile Asn Ala Ser Val Val
1               5                   10                  15

Asn Ile Gln Lys Glu Ile Asp Arg Leu Asn Glu Val Ala Lys Asn Leu
            20                  25                  30

Asn Glu Ser Leu Ile Asp Leu Gln Glu Leu Gly Lys Tyr Glu Gln Tyr
        35                  40                  45

Ile Lys
    50

<210> SEQ ID NO 183
<211> LENGTH: 47
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Gln Ala Leu Asn Thr Leu Val Lys Gln Leu Ser Ser Asn Phe Gly Ala
1               5                   10                  15

Ile Ser Ser Val Leu Asn Asp Ile Leu Ser Arg Leu Asp Lys Val Glu
            20                  25                  30

Ala Glu Val Gln Ile Asp Arg Leu Ile Thr Gly Arg Leu Gln Ser
        35                  40                  45

<210> SEQ ID NO 184
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Pro Asp Val Asp Leu Gly Asp
1               5

<210> SEQ ID NO 185
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Asp Val Asp Leu Gly Asp Ile
1               5

<210> SEQ ID NO 186
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Val Asp Leu Gly Asp Ile Ser
1               5
```

<210> SEQ ID NO 187
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Asp Leu Gly Asp Ile Ser Gly
1               5

<210> SEQ ID NO 188
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Leu Gly Asp Ile Ser Gly Ile Asn
1               5

<210> SEQ ID NO 189
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Gly Asp Ile Ser Gly Ile Asn
1               5

<210> SEQ ID NO 190
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Asp Ile Ser Gly Ile Asn Ala
1               5

<210> SEQ ID NO 191
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Ile Ser Gly Ile Asn Ala Ser
1               5

<210> SEQ ID NO 192
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 192

Ser Gly Ile Asn Ala Ser Val
1               5

<210> SEQ ID NO 193
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Gly Ile Asn Ala Ser Val Val
1               5

<210> SEQ ID NO 194
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Ile Asn Ala Ser Val Val Asn
1               5

<210> SEQ ID NO 195
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Asn Ala Ser Val Val Asn Ile
1               5

<210> SEQ ID NO 196
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Ala Ser Val Val Asn Ile Gln
1               5

<210> SEQ ID NO 197
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Ser Val Val Asn Ile Gln Lys Glu Ile Asp Arg Leu Asn Glu Val Ala
1               5                   10                  15

Lys Asn Leu Asn Glu Ser Leu Ile Asp Leu Gln Glu Leu Gly Lys Tyr
            20                  25                  30
```

-continued

```
Glu Gln Tyr Ile Lys
        35
```